United States Patent
Yokono et al.

(10) Patent No.: US 7,449,213 B2
(45) Date of Patent: Nov. 11, 2008

(54) METHOD FOR MANUFACTURING PLASMA DISPLAY PANEL, INSPECTION METHOD FOR INSPECTING PHOSPHOR LAYER AND INSPECTION APPARATUS FOR INSPECTING PHOSPHOR LAYER

(75) Inventors: Shinji Yokono, Tokyo (JP); Kazumasa Nishiwaki, Tokyo (JP)

(73) Assignee: Pioneer Corporation, Tokyo (JP)

( * ) Notice: Subject to any disclaimer, the term of this patent is extended or adjusted under 35 U.S.C. 154(b) by 628 days.

(21) Appl. No.: 10/611,961

(22) Filed: Jul. 3, 2003

(65) Prior Publication Data
US 2004/0076739 A1 Apr. 22, 2004

(30) Foreign Application Priority Data
Jul. 5, 2002 (JP) ............... 2002-197992

(51) Int. Cl.
*C23C 14/54* (2006.01)
(52) U.S. Cl. ............ 427/10; 427/68; 427/256; 427/372.2
(58) Field of Classification Search ............... 427/9–10, 427/68, 256, 372.2
See application file for complete search history.

(56) References Cited

U.S. PATENT DOCUMENTS

| 4,755,752 A | * | 7/1988 | Fitzpatrick ............ 324/228 |
|---|---|---|---|
| 6,797,975 B2 | * | 9/2004 | Nishiyama et al. ..... 250/559.04 |
| 2002/0009536 A1 | * | 1/2002 | Iguch et al. ............ 427/10 |
| 2002/0038822 A1 | * | 4/2002 | Suzuki et al. ............ 239/101 |
| 2002/0063527 A1 | * | 5/2002 | Hayashi et al. ............ 313/586 |
| 2002/0122174 A1 | * | 9/2002 | Hamamatsu et al. ..... 356/237.2 |

FOREIGN PATENT DOCUMENTS

| JP | 11-16498 A | 1/1999 |
|---|---|---|
| JP | 2000-149781 A | 5/2000 |
| JP | 2000-304651 A | 11/2000 |
| KR | 1999-85889 | 12/1999 |
| KR | 2001-97384 | 11/2001 |
| WO | WO 9827570 | * 6/1998 |

OTHER PUBLICATIONS

Korean Office Action.

* cited by examiner

*Primary Examiner*—Timothy Meeks
*Assistant Examiner*—Jimmy Lin
(74) *Attorney, Agent, or Firm*—Sughrue Mion, PLLC

(57) ABSTRACT

A phosphor paste is applied to inner surfaces of a cell. Then, a conveyer moves a substrate relative to a CCD camera at a constant speed. Simultaneously, two LEDs radiate visible light onto a portion, to be inspected, of the substrate. The visible light is light configured to have a wavelength so as to be able to prevent the phosphor of the phosphor paste from being excited and emitting light and reflected by a liquid surface of the phosphor paste to produce reflected light. Thereafter, the CCD camera captures an image of the phosphor paste and a data processor processes the received image data, and determines whether a phosphor layer formed by drying the phosphor paste will normally be formed, prior to formation of phosphor layer.

6 Claims, 12 Drawing Sheets

FIG. 9

| STATE | BEFORE DRYING | | AFTER DRYING |
| --- | --- | --- | --- |
| | (UPPER SURFACE) | (CROSS SECTION) | (CROSS SECTION) |
| AMOUNT OF PASTE IS EXCESSIVE | | | |
| AMOUNT OF PASTE IS SUITABLE | | | |
| AMOUNT OF PASTE IS SMALL (1) | | | |
| AMOUNT OF PASTE IS SMALL (2) | | | |
| AMOUNT OF PASTE IS LACKING | | | |
| CELL IS EMPTY | | | |

| STATE | BEFORE DRYING (UPPER SURFACE) | AFTER BINARY OPERATION (UPPER SURFACE) |
|---|---|---|
| AMOUNT OF PASTE IS EXCESSIVE |  |  25 |
| AMOUNT OF PASTE IS SUITABLE |  | 25  L |
| AMOUNT OF PASTE IS SMALL (1) |  | 25  L |
| AMOUNT OF PASTE IS SMALL (2) |  | 25  L |
| AMOUNT OF PASTE IS LACKING |  | 25  L, W |
| CELL IS EMPTY |  | 25  L, W |

METHOD FOR MANUFACTURING PLASMA DISPLAY PANEL, INSPECTION METHOD FOR INSPECTING PHOSPHOR LAYER AND INSPECTION APPARATUS FOR INSPECTING PHOSPHOR LAYER

BACKGROUND OF THE INVENTION

1. Field of the Invention

The present invention relates to a method for manufacturing a plasma display panel and an inspection method and apparatus for inspecting a phosphor layer, all of which are conceived to allow inspection during a step of forming a phosphor layer to be performed for a shorter period of time and further to be performed at lower cost.

2. Description of the Related Art

When manufacturing a plasma display panel (hereinafter, referred to also as PDP), components such as a scanning electrode, a sustain electrode and a dielectric layer are formed on one transparent substrate, resulting in formation of a front substrate, and components such as a data electrode, a dielectric layer, a barrier rib and a phosphor layer are formed on the other substrate, resulting in formation of a rear substrate. Then, the front substrate and the rear substrate are aligned to overlap each other and attached together with an adhesive sealing material. Thereafter, gas contained in discharge spaces formed between the front substrate and the rear substrate is evacuated, and the discharge spaces are filled with discharge gas. Thus, a PDP is manufactured.

The rear substrate is manufactured such that data electrodes and a dielectric layer are formed and further barrier ribs are formed on a transparent substrate, and then, a phosphor layer is formed on inner surfaces of a cell that is separated from other cells by the ribs. Phosphors of the phosphor layer are excited with ultraviolet rays generated by discharge within the cell, emitting visible light. A color PDP typically has three types of phosphor layers emitting light of the primary colors, i.e., Red (R), Green (G), Blue (B) respectively and are formed in individual cell columns. That is, one type of phosphor layer is formed in one cell, and cells each having the same type of phosphor layer are arranged in a column. In more detail, a cell column (green cell column) consisting of cells each having a phosphor layer corresponding to G is disposed adjacent a cell column (red cell column) consisting of cells each having a phosphor layer corresponding to R and a cell column (blue cell column) consisting of cells each having a phosphor layer corresponding to B is disposed adjacent the green cell column, and then, a red cell column is disposed adjacent the blue cell column, and further, the above-described arrangement of cell columns is repeated on the rear substrate. The phosphor layers are formed color by color such as by printing techniques and dried, and then, inspected. A conventional method for forming a phosphor layer will be explained below.

FIG. 1 is a side view of a conventional inspection apparatus for inspecting a phosphor layer and FIG. 2 is a partially enlarged cross sectional view of the conventional inspection apparatus for inspecting a phosphor layer. Note that although a rear substrate of PDP has a number of cells arranged in a matrix of rows and columns on a substrate, an enlarged cross sectional view of only one cell is illustrated in FIG. 2 for simplification. Furthermore, illustration of a dielectric layer is omitted in FIG. 2 for simplification. As shown in FIGS. 1 and 2, the conventional inspection apparatus for inspecting a phosphor layer has a conveyer 106 provided therein to move a substrate 1 in one direction. Furthermore, directly above a portion 1a to be inspected on the substrate 1 is provided an ultraviolet ray lamp 102. The ultraviolet ray lamp 102 is provided to radiate ultraviolet rays 104 onto a phosphor layer 5. This allows phosphors of the phosphor layer 5 to be excited and emit excited light 105.

Moreover, two CCD cameras 103a and 103b are provided above the portion 1a and on upstream and downstream sides of the substrate 1 when viewing the conveyer in a direction in which the substrate 1 moves. That is, the two CCD cameras 103a and 103b are disposed so as to interpose the ultraviolet ray lamp 102 therebetween in a direction in which the substrate 1 moves. Note that in order to inspect the phosphor layer 5 formed to cover side surfaces of barrier ribs 2, at least two CCD cameras need to be provided. This is because when trying to capture the image of an object from directly above the portion 1a with one CCD camera, information about the phosphor layer 5 formed on the side surfaces of the ribs 2 cannot be obtained and in a case where the phosphor layer 5 is formed shorter than a desired height and/or has defects such as a void, such abnormal formation of phosphor layer cannot be detected. Therefore, a plurality of sets of one ultraviolet ray lamp 102 and two CCD cameras 103a and 103b are provided along a direction orthogonal to a direction in which the substrate 1 moves. For example, when seven sets of those components need to be provided, totally, 14 CCD cameras are provided.

FIG. 3 is a flow chart diagram illustrating process steps of forming a phosphor layer, which process steps are included in conventional manufacturing steps for PDP. As shown in step S101 of FIG. 3, a phosphor paste of first color (e.g., red) material is applied to inner surfaces of a cell every third column such as by printing techniques. Then, as shown in step S102, for example, the substrate is held in a dry oven for 30 minutes to dry and harden the phosphor paste of red material. Thus, as shown in FIG. 2, a phosphor layer 5 is formed. In this case, barrier ribs 2 having a rectangular lattice-like layout or stripe-like layout are formed on the substrate 1 and a cell 3 is separated from other cells by the ribs 2. Additionally, a data electrode 4 is formed within the cell 3 on the substrate 1 and the phosphor layer 5 is formed on a surface of the substrate 1 and side surfaces of the ribs 2, all surfaces constituting inner surfaces of the cell 3. Thereafter, as shown in step S103, whether or not the phosphor layer 5 is normally being formed within each cell is inspected. A conventional inspection method for inspecting a phosphor layer will be explained below.

First, as shown in FIGS. 1 and 2, the substrate 1 is made to move in one direction by the conveyer 106. At this point, the ultraviolet ray lamp 102 radiates the ultraviolet rays 104 onto the portion 1a of the substrate 1. This allows phosphors of the phosphor layer 5 to be excited and emit the excited light 105. The two CCD cameras 103a and 103b detect the excited light 105. Thus, the image of the phosphor layer 5 is captured. Then, by measuring brightness of the excited light from the phosphor layer 5 based on image data indicative of the image captured as described above, whether the phosphor layer has normally been formed is inspected. When the phosphor layer is determined as containing defects, information indicative of the defects is fed back to the step, shown in step S101, of applying a phosphor paste of red material. The above-described inspection method is disclosed, for example, in Japanese Patent Publication Laid-Open No. Hei 11(1999)-16498, Japanese Patent Publication Laid-Open No. 2000-149781 and Japanese Patent Publication Laid-Open No. 2000-304651.

Subsequently, as shown in step S104, a phosphor paste of second color (e.g., green) material is applied to a cell column adjacent the cell column on which the red phosphor layer is formed. Then, as shown in step S105, the phosphor paste of green material is dried and hardened to form a green phosphor layer. Thereafter, as shown in step S106, whether the green phosphor layer has normally been formed is inspected. An inspection apparatus and method for inspecting a phosphor layer is the same as that employed to inspect the red phosphor layer. When the phosphor layer is determined as containing defects, information indicative of the defects is fed back to the step, shown in step S104, of applying a phosphor paste of green material. Then, as shown in step S107, a phosphor paste of third color (e.g., blue) material is applied to a cell column adjacent the cell column on which the green phosphor layer is formed. Thereafter, as shown in step S108, the phosphor paste of blue material is dried and hardened to form a blue phosphor layer. Then, as shown in step S109, whether the blue phosphor layer has normally been formed is inspected. When the phosphor layer is determined as containing defects, information indicative of the defects is fed back to the step, shown in step S107, of applying a phosphor paste of blue material. Note that the reason why the inspection operation is performed on individual columns corresponding to individual colors as described above is that making the phosphor layers emit light of individual colors at the same brightness level and simultaneously inspecting the phosphor layers is difficult to implement.

However, the aforementioned conventional techniques include the following problems. First, since the step of inspecting a phosphor layer is performed after drying of phosphor layer, a timing for feeding back results obtained by the inspection to the application step of applying a phosphor paste is unfavorably delayed. That is, when defects are created in the application step (e.g., step S101) of applying a phosphor paste, at least a time interval required for completion of a dry step (step S102), for example, 30 minutes elapses until the defects are detected in the inspection step (step S103) and therefore, an empty time during which the results obtained by the inspection are not fed back to the application step of applying a phosphor paste occurs. Accordingly, in some cases, products having the same types of defects are sequentially manufactured during this empty time, resulting in significant reduction in PDP production yield.

Furthermore, the use of the aforementioned conventional technique unfavorably increases the investment cost of inspection apparatus. That is, in the conventional inspection apparatus shown in FIG. 1, the ultraviolet ray lamp 102 is employed and therefore, a countermeasure to prevent an operator from directly viewing the ultraviolet rays has to be implemented. Moreover, since the ultraviolet rays react with oxygen in an atmosphere, creating harmful ozone, the inspection apparatus needs to be configured as a sealed unit and then evacuated or to be configured to have an area, onto which ultraviolet rays are radiated, placed in a nitrogen atmosphere, as described in Japanese Patent Publication Laid-Open No. Hei 11(1999)-16498. Additionally, as stated above, the conventional inspection apparatus needs to have two CCD cameras provided therein. Furthermore, when inspecting a specific color (e.g., blue) phosphor layer, a CCD camera needs to have a filter mounted on a lens of the camera in order to prevent light from the excited phosphors of a phosphor layer (e.g., red or green) that is formed prior to formation of the specific phosphor layer from interfering with light from the excited phosphors of the specific phosphor layer and then capture only the desired color (in this case, blue), as shown in Japanese Patent Publication Laid-Open No. 2000-149781. As a result, the investment cost of inspection apparatus is increased.

Furthermore, running cost of inspection apparatus unfavorably becomes high. An ultraviolet ray lamp has a lifetime nearly equal to that of a typical illumination device such as a fluorescent lamp, a halogen lamp and an LED, but is expensive. Moreover, as stated above, an equipment for preventing generation of ozone needs to be provided in the inspection apparatus, adding the running cost of the equipment to the inspection apparatus.

Still furthermore, a micron-sized defect such as a pinhole and an abnormal substance included in a phosphor layer is detected by capturing the image of a portion emitting light at a low brightness level and created within a cell according to the conventional inspection method. However, when employing the conventional inspection method, since the captured image is constructed such that a gray scale indicative of light intensity corresponding to the pinhole and a gray scale indicative of light intensity corresponding to the abnormal substance are nearly equal to each other, whether the captured image represents the pinhole or the abnormal substance cannot be determined.

SUMMARY OF THE INVENTION

An object of the present invention is to provide a method for manufacturing a plasma display panel and an inspection method and apparatus for inspecting a phosphor layer, all of which include an inspection step that allows operation for quickly feeding back results obtained by inspecting a phosphor layer to an application step of applying a phosphor material while allowing identification of types of defects and permitting investment cost and running cost to become low.

A method for manufacturing a plasma display panel according to a first aspect of the invention comprises the steps of: forming barrier ribs on a surface of an insulating substrate in order to separate a plurality of cells from one another; applying a phosphor material in the form of paste to a surface of the insulating substrate and side surfaces of the ribs; and, radiating light onto a surface of the phosphor material prior to drying the phosphor material and observing a pattern of light reflected from each of the plurality of cells in order to inspect whether a phosphor material is normally being applied to each of the plurality of cells.

The method according to the first aspect of the invention is performed such that after the phosphor material is applied in the form of paste to the surface of the insulating substrate and the side surfaces of barrier ribs, and prior to drying the phosphor material, whether the phosphor material is normally being applied to associated portions is inspected.

In this case, the surface of the phosphor material specularly reflects light incident thereon and therefore, the inspection operation can be performed not using excited light but using reflected light. Furthermore, since the pattern of reflected light faithfully describes a situation in which the liquid surface of phosphor material is being formed, the state indicative of a situation in which the phosphor material is being applied can be inspected by inspecting the pattern of reflected light.

In this case, the situation in which the phosphor material is being applied and determination whether the phosphor layer after drying of the phosphor material is normally being formed or not have a strong correlative relationship therebetween, and therefore, inspection of a situation in which the phosphor material before drying of the phosphor material is being applied makes it possible to determine whether the phosphor layer after drying of the phosphor material will normally be formed or not. This allows determination of whether the phosphor layer will normally be formed or not to be performed before drying of the phosphor material and therefore, allows the results obtained by determination of whether the phosphor layer will normally be formed or not to quickly be fed back to the step of applying a phosphor material. Furthermore, observing the pattern of reflected light permits identification of types of defects. Moreover, there is no need to employ an ultraviolet ray lamp as a light source. That is, employment of the invention eliminates the need for an ultraviolet ray lamp, an apparatus for preventing an operator from directly viewing the ultraviolet ray and an equipment for preventing generation of ozone, thereby allowing investment cost and running cost of the associated apparatus equipment to become low.

Furthermore, the inspection step of inspecting whether a phosphor material is normally being applied to each of the plurality of cells may includes the steps of: capturing an image of the applied phosphor material while radiating light onto a surface of the applied phosphor material in order to obtain image data indicative of the image of the applied phosphor material; distinguishing patterns of images each consisting of light reflected from each of the plurality of cells from one another based on the image data; and inspecting whether the phosphor material is normally being applied to each of the plurality of cells based on results obtained by distinguishing the patterns from one another in order to determine whether or not a phosphor layer formed by drying the phosphor material will normally be formed.

Alternatively, the inspection step of inspecting whether a phosphor material is normally being applied to each of the plurality of cells may includes the steps of: detecting micro-defects defined as a defect included in each of the plurality of cells; and detecting macro-defects defined as a defect included in each of blocks consisting of a plurality of cells. This allows micro-defects as defects included in each of a plurality of cells to be detected and at the same time, permits macro-defects as defects included in each block consisting of a plurality of cells to be detected. As a result, uneven display on a screen of PDP can be identified as a defect, allowing determination operation to be performed so as to produce results nearly equivalent to those obtained by visual determination.

Additionally, the method according to the invention is carried out such that the phosphor material is employed as one of a plurality of phosphor materials corresponding to a plurality of colors and one of the plurality of phosphor materials is excited and emits light of one of the plurality of colors, and the inspection step of inspecting a phosphor material is performed a plurality of times to allow the method to include a plurality of inspection steps corresponding to the plurality of colors of excited lights emitted from the plurality of phosphor materials, and further, on and after the second inspection step, whether or not a phosphor layer will normally be formed is determined based on results obtained in a current inspection step chosen out of the plurality of inspection steps and currently being performed, and results obtained in the inspection steps performed before the current inspection step. Accordingly, the defects that cannot easily be detected through a single inspection step can be detected.

Moreover, the method according to the invention may be carried out such that the light is light having a wavelength range so as to be able to prevent the phosphor material from being excited and emitting light. Accordingly, the pattern produced only by reflected light can accurately be observed without interference from the excited light.

An inspection method, according to a second aspect of the invention, for inspecting a phosphor layer, which is formed by applying a phosphor material in the form of paste to a surface of an insulating substrate whose surface is divided into a plurality of cells and drying the phosphor material, comprises: observing a pattern of light reflected from each of the plurality of cells while radiating light onto a surface of the phosphor material, after application of the phosphor material to the substrate and prior to drying the phosphor material, in order to inspect whether a phosphor material is normally being applied to each of the plurality of cells and then determine whether or not the phosphor layer will normally be formed.

An inspection apparatus, according to a third aspect of the invention, for inspecting a phosphor layer, which is formed by applying a phosphor material in the form of paste to a surface of an insulating substrate whose surface is divided into a plurality of cells and drying the phosphor material, comprises: a light source disposed above the substrate and illuminating the phosphor material being applied in the form of paste; a camera disposed above the substrate and capturing an image of the phosphor material being applied; and a data processor for identifying a pattern of light reflected from each of the plurality of cells based on image data indicative of the image of the phosphor material captured by the camera and inspecting whether the phosphor material is normally being applied to each of the plurality of cells in order to determine whether or not the phosphor layer will normally be formed.

Preferably, the inspection apparatus is further constructed such that the camera may be disposed directly above the phosphor material whose image is to be captured by the camera and the light source may be employed as one of two light sources and the two light sources are disposed so as to interpose the camera therebetween. Accordingly, the cameras are able to capture an image of light scattered by the phosphor material with higher efficiency and further capture clearer reflected light patterns.

As described above, according to the invention, whether the phosphor layer will normally be formed can be determined prior to drying the phosphor material and therefore, results obtained by determination of whether the phosphor layer will normally be formed or not can quickly be fed back to the step of applying a phosphor material. Furthermore, since inspection of whether the phosphor material is normally being applied is performed based on the pattern of reflected light, ultraviolet rays need not to be employed, allowing investment cost and running cost of the associated apparatus equipment to become low. Moreover, observation of the pattern of reflected light allows identification of types of defects.

BRIEF DESCRIPTION OF THE DRAWINGS

FIG. 9 is a schematic diagram illustrating defects detected using the inspection method according to the embodiment;

FIGS. 10A to 10C are schematic diagrams illustrating defects detected using the inspection method according to the embodiment, wherein FIG. 10A illustrates a pinhole included in a cell, FIG. 10B illustrates a situation in which a phosphor material flows into a cell, and FIG. 10C illustrates an abnormal substance included in a cell;

DETAILED DESCRIPTION OF THE PREFERRED EMBODIMENT

As described above, in the conventional manufacturing steps for PDP, a phosphor paste is applied to the dielectric layer on the insulating substrate and dried to form the phosphor layer, and then, the phosphor layer is inspected. The dielectric layer formed on the insulating substrate is imaged as a white image and the ribs also are imaged as a white image, and further, the phosphor layer placed in a situation in which the phosphor layer is not emitting excited light is imaged as a white image. Accordingly, those components cannot be distinguished from one another by use of reflected light and conventionally, inspecting a phosphor layer by use of reflected light has been considered impossible. To solve the above-mentioned problem, inspection of phosphor layer has conventionally been performed by radiating ultraviolet rays onto a phosphor layer and making the phosphor layer emit excited light corresponding to each of individual colors. As a result, various problems have been arising as described above when ultraviolet rays are employed. Furthermore, a timing for feeding back the results obtained by inspection to the application step of applying a phosphor paste is unfavorably delayed.

In order to solve the above-described problems, the inventors of this application have energetically and repeatedly studied and experimented, and finally found the following facts, allowing the inventors to complete the present invention. That is, when trying to capture the image of phosphor paste, which are applied to individual cells, prior to drying the phosphor paste, the phosphor paste is still being in the form of paste and specularly reflects light incident thereon, and patterns of images of the reflected light indicative of a profile of a liquid surface of the paste are obtained. In this case, the profile of the liquid surface of the phosphor paste depicts a situation in which the paste is being applied and the situation in which the phosphor paste is being applied and determination whether the phosphor layer after drying of the paste will normally be formed or not have a strong correlative relationship therebetween, and therefore, the patterns of images of the reflected light give a tool to determine whether the phosphor layer after drying of the paste is normally being formed or not.

Figure 4:
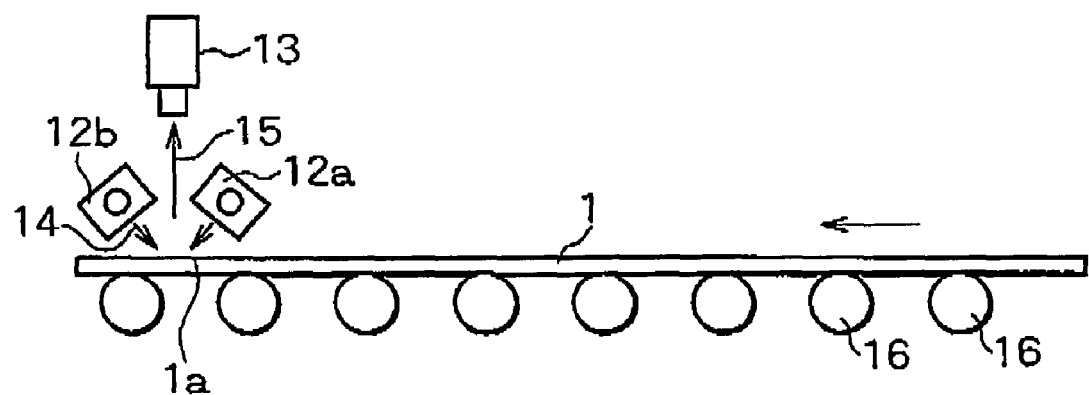
FIG. 4 is a side view of an inspection apparatus for inspecting a phosphor layer according to an embodiment of the invention.

Embodiments of the present invention will be explained in detail below with reference to the attached drawings. FIG. 4 is a side view of an inspection apparatus for inspecting a phosphor layer according to an embodiment. As shown in FIG. 4, the inspection apparatus for inspecting a phosphor layer according to the embodiment is configured to have a conveyer 16 provided to move a substrate 1 that is to be a rear substrate of PDP in one direction. The substrate 1 is made of, for example, glass. Furthermore, Light Emitting Diodes (LEDs) 12a and 12b are provided above a portion 1a to be inspected on the substrate 1 and on upstream and downstream sides of the substrate 1 when viewing the conveyer in a direction in which the substrate 1 moves. The LEDs 12a and 12b are disposed to extend in a direction orthogonal to a direction in which the substrate 1 moves and the length of the LED is nearly equal to a width of the substrate 1, which width extends in a direction orthogonal to a direction in which the substrate 1 moves. The LEDs 12a and 12b are provided to approximately uniformly radiate visible light 14 onto the portion 1a of the substrate 1. Note that instead of LED, other typical illumination devices such as a fluorescent lamp and a halogen lamp may be employed.

Moreover, a CCD camera 13 is provided directly above the portion 1a of the substrate 1. The CCD camera 13 may be a monochrome camera producing one-dimensional images having resolutions of 8,000 dots per inch and capturing reflected light 15 from the portion 1a. In the embodiment, the CCD camera 13 is able to capture an image with a resolution of 20 μm by 20 μm at the surface of the substrate 1. Then, a plurality of CCD cameras 13, for example, seven CCD cameras are provided along a direction orthogonal to a direction in which the substrate 1 moves. In this case, the portion 1a is disposed within overall fields of view of the seven CCD cameras 13. Still furthermore, a data processor (not shown) for processing image data indicative of an image captured by the CCD camera 13 and determining whether a phosphor layer will normally be formed or not is provided and connected to the CCD cameras 13.

Figure 5:
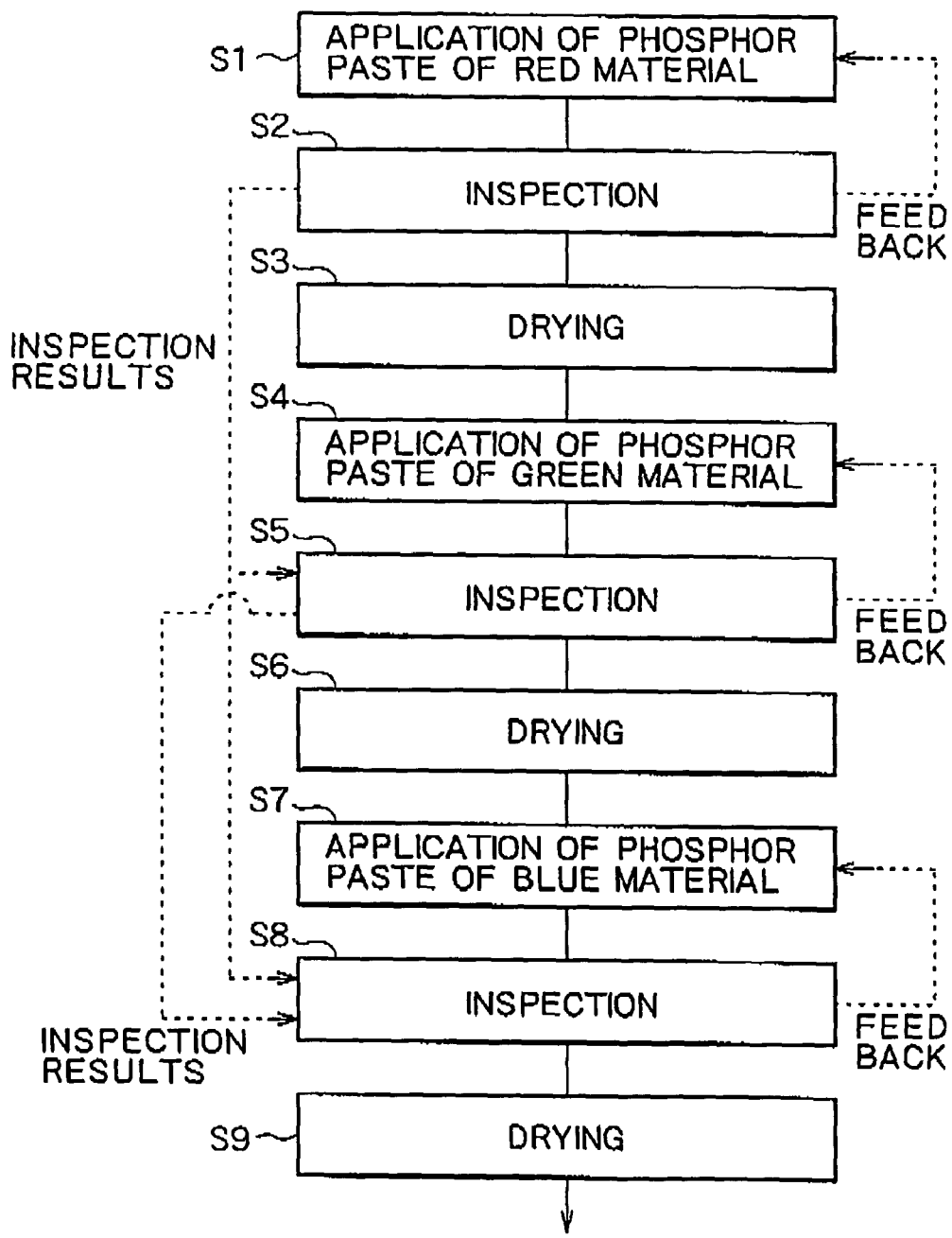
FIG. 5 is a flow chart diagram illustrating process steps of forming a phosphor layer according to the embodiment, which process steps are included in manufacturing steps for a PDP.
Figure 6:
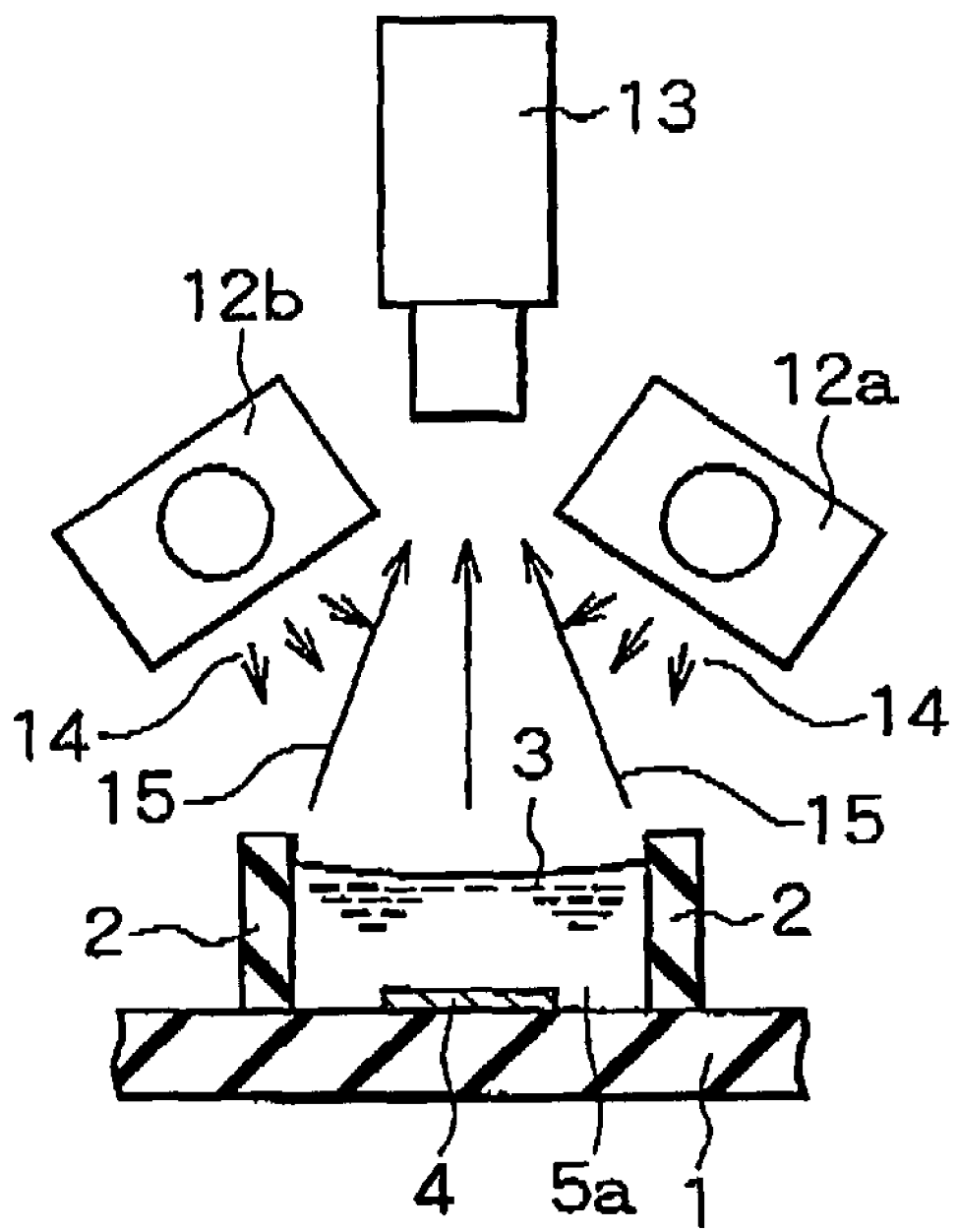
FIG. 6 is a cross sectional view illustrating how a phosphor layer is inspected according to the embodiment.
Figure 7:
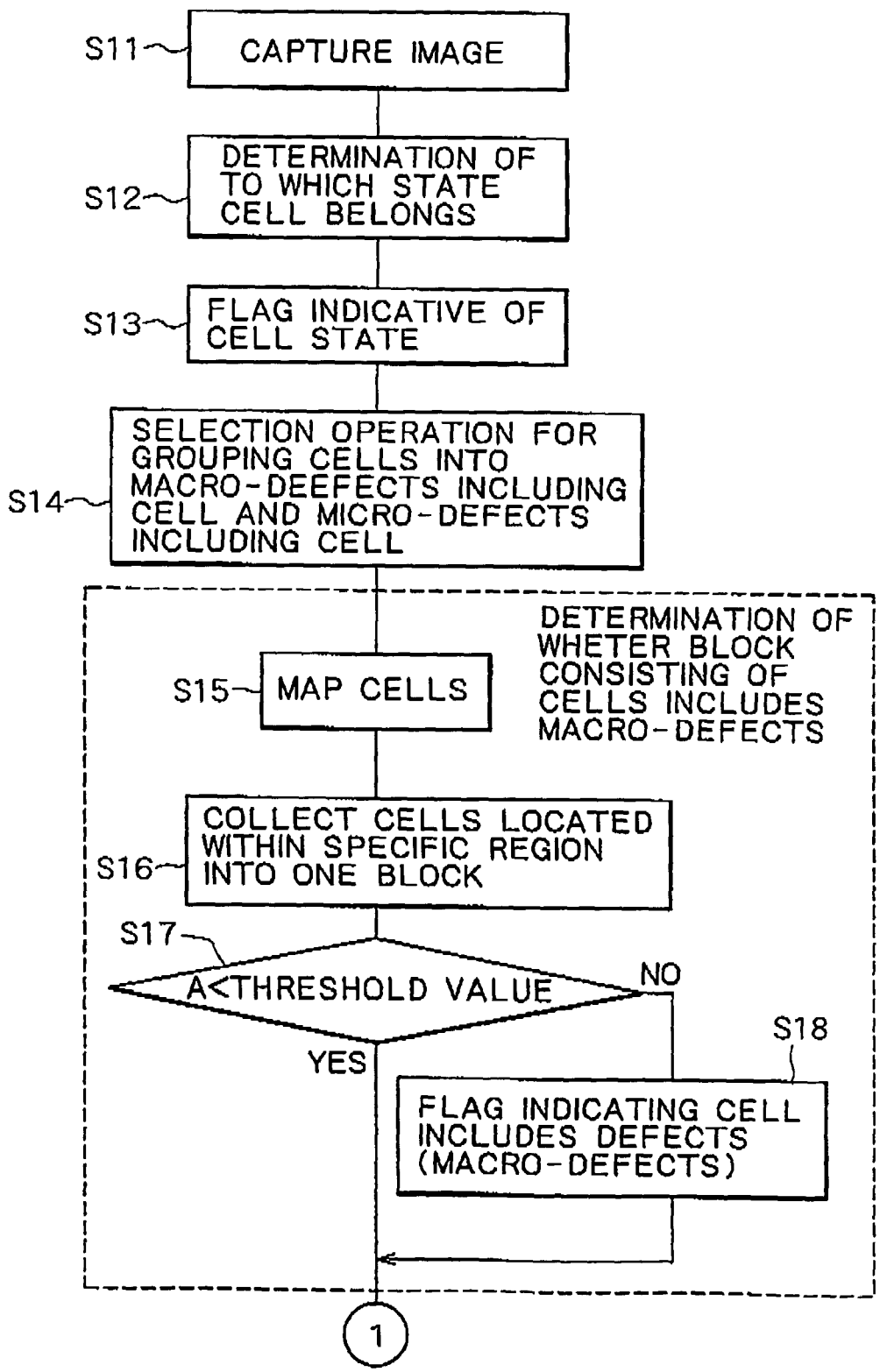
FIG. 7 is a flow chart diagram illustrating how a phosphor layer is inspected according to the embodiment.
Figure 8:
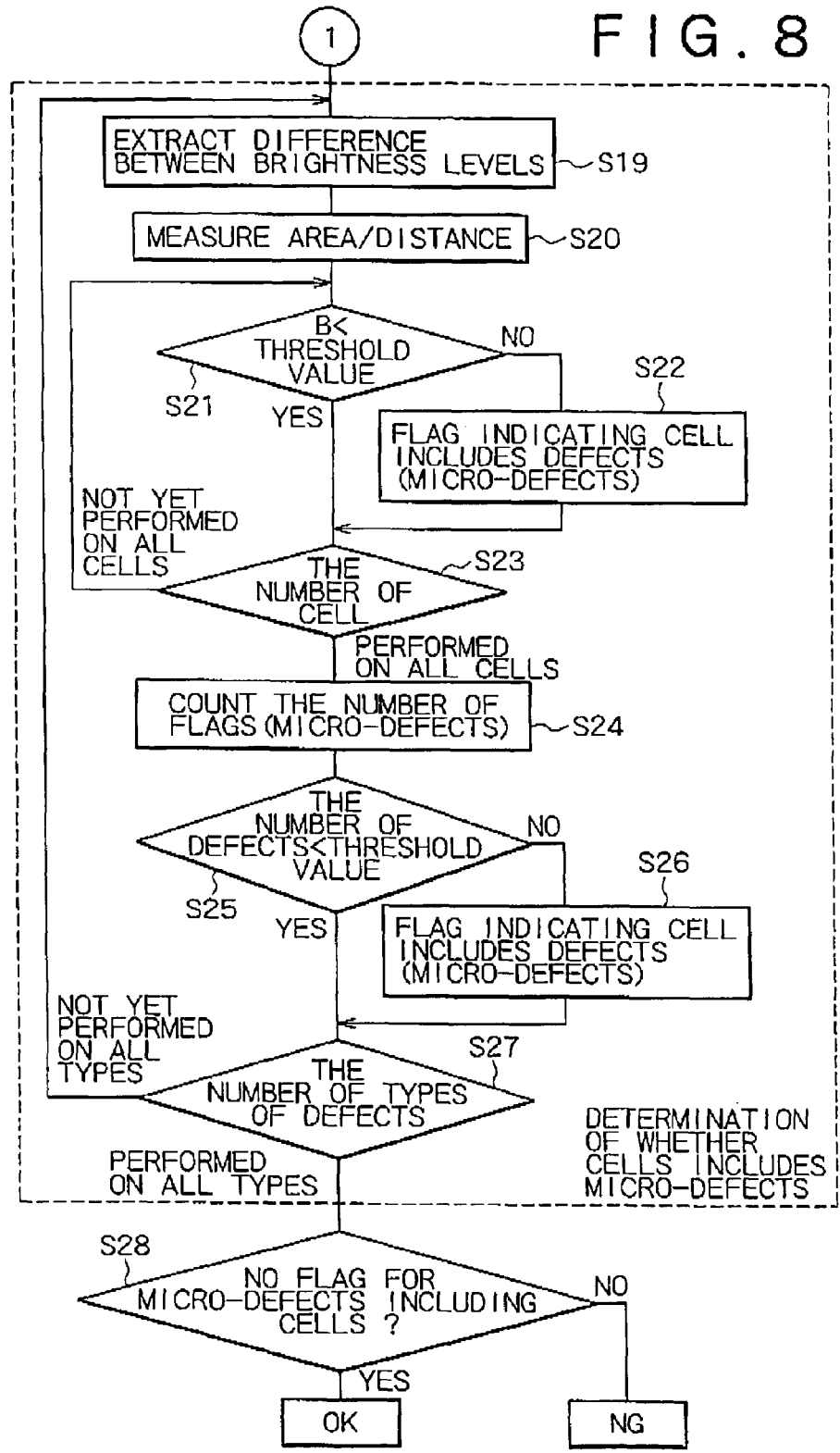
FIG. 8 is a flow chart diagram illustrating how a phosphor layer is inspected according to the embodiment, wherein the flow chart is subsequent to the flow chart of FIG. 7.
Figure 11:
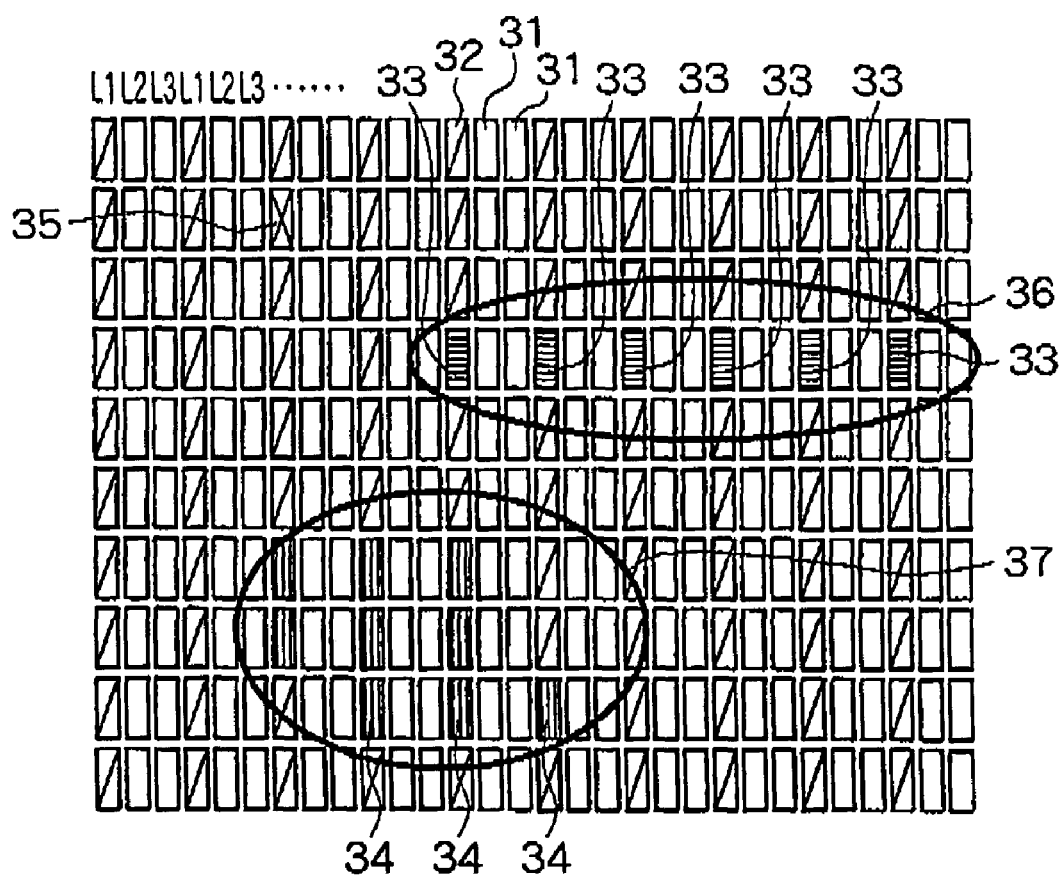
FIG. 11 is a diagram illustrating how cells are mapped according to the embodiment.
Figure 12:
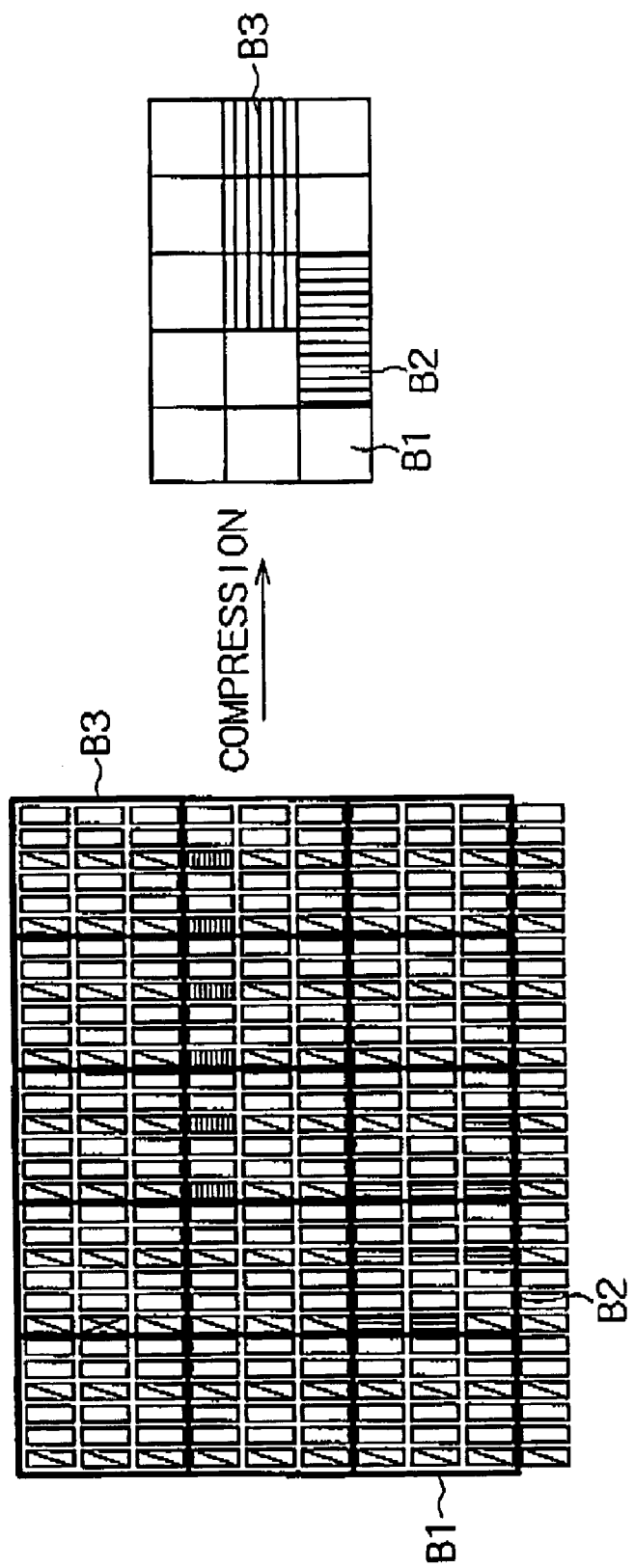
FIG. 12 is a diagram illustrating how cells are grouped into individual blocks according to the embodiment.
Figure 13:
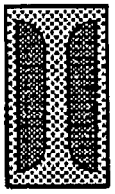
FIG. 13 is a diagram illustrating the step of extracting a difference between brightness levels according to the embodiment.
Figure 13:
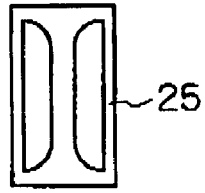
Figure 13:
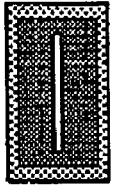
Figure 13:
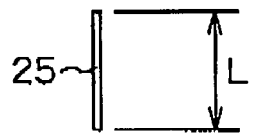
Figure 13:
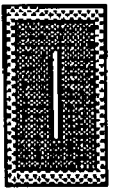
Figure 13:
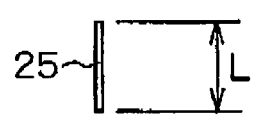
Figure 13:
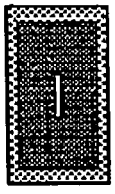
Figure 13:
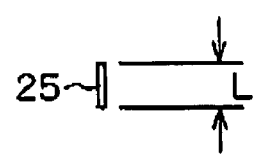
Figure 13:
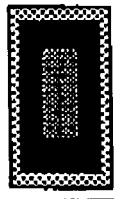
Figure 13:
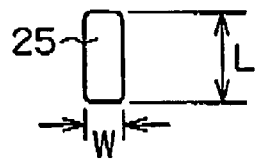
Figure 13:
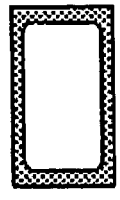
Figure 13:
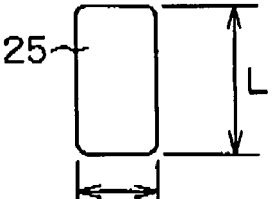

Subsequently, a method, including an inspection method for inspecting a phosphor layer, for manufacturing a PDP according to the embodiment will be explained. FIG. 5 is a flow chart diagram illustrating process steps of forming a phosphor layer according to the embodiment, which process steps are included in manufacturing steps for a PDP. FIG. 6 is a cross sectional view illustrating how a phosphor layer is inspected according to the embodiment. FIGS. 7 and 8 are flow chart diagrams illustrating how a phosphor layer is inspected according to the embodiment. FIGS. 9 and 10A-10C are schematic diagrams illustrating defects detected using the inspection method according to the embodiment. FIG. 11 is a diagram illustrating how cells are mapped according to the embodiment. FIG. 12 is a diagram illustrating how cells are grouped into individual blocks according to the embodiment. FIG. 13 is a diagram illustrating the step of extracting a difference between brightness levels according to the embodiment. Note that although a rear substrate of PDP has a number of cells arranged in a matrix of rows and columns thereon, only one cell magnified is depicted in FIG. 6. Furthermore, illustration of dielectric layer is omitted in FIG. 6 for simplification, First, a plurality of scanning electrodes and a plurality of sustain electrodes are formed on a transparent substrate so that the scanning electrodes and the sustain electrodes extend in parallel with one another and alternately disposed. Then, a dielectric layer is formed to cover the scanning electrodes and the sustain electrodes, thereby preparing a front substrate.

On the other hand, data electrodes and a dielectric layer are formed on a surface of the other transparent substrate and then barrier ribs are formed. The rib structure has, for example, a rectangular lattice-like layout and the space between the ribs defines each of the cells arranged in a matrix of rows and columns. Note that one cell is formed to have a length of, for example, 400 to 1100 μm in a direction of major side of cell and a length of, for example, 200 to 300 μm in a direction of minor side of cell. Thereafter, a phosphor layer is formed on inner surfaces of a cell separated from other cells by the ribs. Phosphors of the phosphor layer are excited by radiation of ultraviolet rays that are generated by discharge within the cell and then emit light. Like the conventional PDP as described above, in the embodiment, a PDP has three types of phosphor layers emitting light of the primary colors, i.e., Red (R), Green (G), Blue (B), respectively and are formed in individual cell columns. That is, one type of phosphor layer is formed in one cell, and cells each having the same type of phosphor layer are arranged in a column. In more detail, a cell column (green cell column) consisting of cells each having a phosphor layer corresponding to G is disposed adjacent a cell column (red cell column) consisting of cells each having a phosphor layer corresponding to R and a cell column (blue cell column) consisting of cells each having a phosphor layer corresponding to B is disposed adjacent the green cell column, and then, a red cell column is disposed adjacent the blue cell column, and further, the above-described arrangement of cell columns is repeated on the rear substrate. A method for forming phosphor layers will be explained below.

First, referring to step S1 of FIG. 5 and to FIG. 6, a phosphor paste 5a of first color (e.g., red) material is applied to inner surfaces of a cell 3, i.e., the surface of the substrate 1 and side surfaces of the ribs 2, every third column such as by printing techniques. Then, as shown in step S2, for example, whether or not the phosphor paste 5a is normally being applied to the associated portions within each cell 3 is inspected. How the phosphor paste 5a is inspected in step S2 will be explained in detail below.

As shown in step S11 of FIG. 7 and in FIG. 4, the substrate 1 is made to move relative to th CCD camera 13 at a constant speed by the conveyer 16. During movement of the substrate 1, LEDs 12a and 12b radiate visible light 14 to the portion 1a to be inspected on the substrate 1. The visible light 14 is configured to have a wavelength so as not to make phosphors of the phosphor paste 5a excited and then emit light and the visible light is reflected by the liquid surface of the phosphor paste 5a to produce reflected light 15. Then, the CCD camera 13 captures the image of the portion 1a. In this case, the substrate 1 is made to move by the conveyer 16 so that entire surfaces of the substrate 1 pass directly below the CCD camera 13 and the image of the entire surfaces of the substrate 1 is captured by the camera. Furthermore, a data processor (not shown) processes image data indicative of the image captured by the CCD camera 13 and determines whether a phosphor layer that is to be formed by drying phosphor paste will normally be formed. How the image captured as described above is processed will be explained below. Steps S12 to S18 shown in FIG. 7 and steps S19 to S28 shown in FIG. 8 all are performed by the data processor.

First, as shown in step 512 of FIG. 7, the data processor determines whether the phosphor paste 5a is normally being applied to associated portions within each cell based on a pattern of light reflected from each cell, which pattern is produced using the image data indicative of the captured image. If the amount of the phosphor paste 5a applied to associated portions within a cell is suitable and the phosphor paste 5a is uniformly being applied thereto, the pattern of light reflected from the cell becomes a pattern positioned at the cross point of a row "suitable amount" and a sub-column "upper surface" of a column "before drying" of FIG. 9.

Drawings shown in the sub-column "upper surface" of the column "after drying" of FIG. 9 indicate the intensity of the reflected light 15 and an outline region 21 on a colored background indicates a region corresponding to the maximum intensity of the reflected light 15, i.e., a bright region. Furthermore, regions 22, 23 and 24 correspond to the gradually reducing intensity of the reflected light 15 in this order and the region 24 corresponds to the lowest intensity thereof, i.e., a region viewed as a dark region. When the phosphor paste 5a is normally being applied to associated portions within the cell 3, the liquid surface of the phosphor paste 5a is curved in a direction of minor side of the cell 3 and slightly depressed. Accordingly, the liquid surface of the phosphor paste 5a becomes parallel to the surface of the substrate 1 in the central portion of the cell 3 in a direction of minor side thereof and when viewing the cell 3 from the CCD camera 13 positioned directly above the cell, the intensity of the reflected light 15 becomes high in the central portion of the cell 3 in a direction of minor side thereof. Thus, a rectangular and bright region 21 extending in a direction of major side of the cell 3 appears in the central portion of the cell 3 in a direction of minor side thereof.

In contrast, when the amount of the phosphor paste 5a applied to associated portions within a cell is excessive, the pattern of light reflected from the cell becomes a pattern shown in drawings in a row "amount of paste is excessive" of FIG. 9. Furthermore, when the amount of the phosphor paste 5a applied to associated portions within a cell is smaller than a desired amount, the length of a bright region 21 within the pattern of light reflected from the cell becomes shorter in a direction of major side of the cell 3, as shown in drawings in rows "amount of paste is small (1)" and "amount of paste is small (2)" of FIG. 9. This phenomenon can be explained as follows. That is, since the end portions of the liquid surface of the phosphor paste 5a are fixed to the upper ends of the barrier ribs 2, when the amount of the phosphor paste 5a becomes smaller, the extent to which the liquid surface is depressed becomes larger. Moreover, when the amount of the phosphor paste 5a becomes further smaller and then the end portions of the liquid surface of the phosphor paste 5a come not to be fixed to the upper ends of the barrier ribs 2, the entire surface is lowered in height and the intensity of the reflected light 15 becomes weakened, and then the bright region 21 disappears, as shown in drawings in row "amount of paste is lacking" of FIG. 9. Note that in step S12, the cells corresponding to the columns "amount of paste is small (1)," "amount of paste is small (2)," and "amount of paste is lacking" are not necessarily distinguished from one another.

Figure 10A:
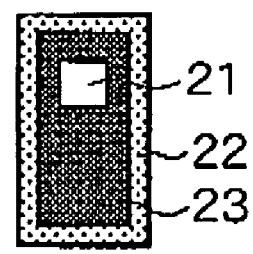
Figure 10B:
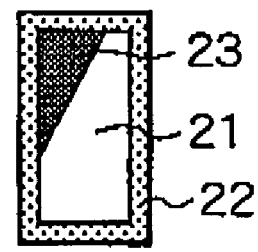
Figure 10C:
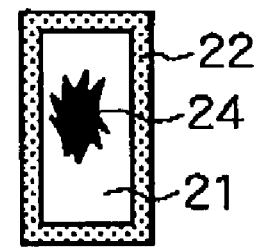

Still furthermore, when the amount of the phosphor paste 5a is extremely small or no phosphor paste is applied, the pattern of light reflected from the cell becomes patterns shown in FIGS. 10A and 10B or reflection patterns shown in rows "cell is empty" or "amount of paste is lacking" of FIG. 9. When cells to which a phosphor paste has been applied are considered as being in the aforementioned states, the cells being in any one of the aforementioned states are all identified as containing "pinholes."

It should be appreciated that in this case, cells to which the phosphor paste 5a is not applied, that is, cells to which a phosphor paste of second and third color (e.g., green and blue) material will be applied by printing techniques in a subsequent step also are inspected. As a result, when a cell is in a normal state, i.e., does not have the phosphor paste 5a applied thereto, the reflection pattern corresponding to the cell becomes the pattern shown as the drawing in the row "cell is empty" of FIG. 9. In contrast, when the phosphor paste 5a has flowed into the cell, the pattern of light reflected from the cell becomes a reflection pattern shown in FIG. 30B. The phosphor paste 5a having flowed into the cell potentially causes color mixture (color smearing) and relative positional displacement. Furthermore, when abnormal substances are mixed within the cell, the pattern of light reflected from the cell becomes a reflection pattern shown in FIG. 10C.

Subsequently, as shown in step S13 of FIG. 7, flags corresponding to individual states (hereinafter, referred to also as a cell state) indicative of a situation in which the phosphor paste 5a is being applied to associated portions of a cell are set in cells other than normal cells, i.e., in cells (hereinafter, referred to as a non-normal cell) that potentially contain defects, based on results obtained by determination in step S12. That is, in step S13, cell states are distinguished from one another. This operation is pre-processing for determination of whether a cell is defective, which determination will be made in later described steps S15 to S27. Furthermore, determination of cell state in step S13 makes it possible to reduce the amount of data processing to be performed in later described steps S19 to S21.

Subsequently, as shown in step S14, non-normal cells in which flags have been set in step S13 are grouped into a micro-defects including cell group and a macro-defects including cell group. The term "micro-defects" represents a cell state which is defined such that a defective state can be identified when defects occur in only one cell and the defects contained in a cell in a defect mode are typified by "pinhole," "color smearing" and "abnormal substance." The cell in this defect mode corresponds to the cell states denoted in the rows "amount of paste is small (2)," "amount of paste is lacking," and "cell is empty" of FIG. 9, and the cell states shown in FIGS. 10A, 10B and 10C. The term "macro-defects" represents a cell state which is defined such that a defective state cannot be identified even when defects occur in only one cell, but a defective state can be identified when defects are concentrated in cells in a specific region within a PDP and appear as uneven display or color distortion, which are determined by visual examination. The cell in this cell state corresponds to the drawings shown in the rows "amount of paste is excessive," "amount of paste is small (1)," and "amount of paste is small (2)," of FIG. 9, and the drawing "paste has flowed into cell" of FIG. 10B.

Thereafter, in steps S15 to S18, determination of whether a block consisting of cells includes macro-defects is carried out. As shown in step S15 and in FIG. 11, processing results obtained in step S13 are mapped. FIG. 11 illustrates cell states corresponding to cells arranged in a matrix of rows and columns and one rectangle represents one cell. A column L1 represents a column of cells to which a phosphor paste of red material is applied in the aforementioned step S1 (refer to FIG. 5) and columns L2 and L3 each represent a column of cells to which a phosphor paste is not yet applied. Accordingly, for the cells constituting the column L1, the cell state corresponding to the row "amount of paste is suitable" of FIG. 9 is normal and for the cells constituting the columns L2 and L3, the cell state corresponding to the row "cell is empty" of FIG. 9 is normal. In FIG. 11, an outline cell 31 on a colored background corresponds to the row "cell is empty." Furthermore, a cell 32 marked with diagonal lines corresponds to the row "amount of paste is suitable." Moreover, a cell 33 marked with horizontal lines corresponds to the row "amount of paste is excessive" and a cell 34 marked with vertical lines corresponds to the rows "amount of paste is small (1)" and "amount of paste is small (2)," and a cell 35 marked with "X" letter corresponds to the "abnormal substance" containing cell. Additionally, a region 36 represents a region in which the cells 33 corresponding to the row "amount of paste is excessive" are concentrated and a region 37 represents a region in which the cells 34 corresponding to the rows "amount of paste is small (1)" and "amount of paste is small (2)" are concentrated.

Subsequently, as shown in step S16 and FIG. 12, map data produced in step S15 is compressed and grouping operation is performed on the map data. The grouping operation is processing for collecting cells located within a specific region into one block and attaching to the block a label that is representative of cell states corresponding to individual cells constituting the block. As shown in FIG. 12, in the embodiment, a set of 18 cells in three rows and six columns constitute one block. Note that the block is not limited to the rectangular size (three rows and six columns) and therefore, may be of a suitable size that allows determination operation to be performed so as to produce results nearly equivalent to those obtained by visual determination. Note that the drawing on the left in FIG. 12 is the same as that of FIG. 11.

For instance, in a block B1, since individual cells constituting the block B1 are all in a normal state, the block B1 is made to have a label "normal" attached thereto. Furthermore, in a block B2, since five cells out of cells constituting the block B2 are in the states corresponding to the rows "amount of paste is small (1)" and "amount of paste is small (2)," the block B2 is made to have a label "amount of paste is small" attached thereto. Moreover, in a block B3, since two cells out of cells constituting the block B3 are in the states corresponding to the row "amount of paste is excessive," the block B3 is made to have a label "amount of paste is excessive" attached thereto.

Thereafter, as shown in step S17, among the non-normal blocks attached with labels other than the label "normal," the number of the non-normal blocks consecutively arranged is assumed to be "A" and the number "A" is compared with a previously determined threshold value, and if the number "A" of the non-normal blocks consecutively arranged is less than the threshold value, the corresponding substrate is determined as "containing no macro-defects," and then, the processing operation proceeds to the next step S19 shown in FIG. 8. In contrast, if the number "A" of the non-normal blocks consecutively arranged is not less than the threshold value, the substrate is determined as "containing macro-defects" and the processing operation proceeds to the next step S18, and then, a flag indicative of inclusion of defects is set in the substrate. Thereafter, the processing operation proceeds to step S19 shown in FIG. 8. For example, since two blocks attached with the label "amount of paste is small" are consecutively arranged, the number "A" of non-normal blocks consecutively arranged is two and since three blocks attached with the label "amount of paste is excessive," are consecutively arranged, and therefore, it can be concluded that the number "A" of non-normal blocks consecutively arranged is three. Note that the threshold value may be changed depending on types of cell states.

Then, as shown in steps S19 to S27 of FIG. 8, determination of whether a cell includes micro-defects is carried out. The determination of whether a cell includes micro-defects is carried out for individual types of defects. As shown in step S19 and FIG. 13, a processing operation for extracting a difference between brightness levels is performed on the reflection patterns obtained in step S12 of FIG. 7 and corresponding to the individual cells. The processing operation for extracting a difference between brightness levels is, for example, a binary operation. The binary operation allows the reflection patterns shown in a column "before drying (upper surface)" of FIG. 13 to be converted into drawings shown in a column "after binary operation (upper surface)."

Subsequently, as shown in step S20 of FIG. 8, the geometrical profile of bright regions 25 in the drawings after binary operation is evaluated. For instance, when the geometrical profile of the bright regions 25 is a rectangle, the cell is considered to be in any one of cell states corresponding to rows "amount of paste is suitable," "amount of paste is small (1)," "amount of paste is small (2)," "amount of paste is lacking," and "cell is empty," as shown in FIG. 13. Then, the length L and width W of the region 25 are measured to calculate the area "B" (=L×W) of the region 25.

Thereafter, as shown in step S21, the area "B" of the region 25 is compared with a previously determined threshold value, and if the area "B" is less than the threshold value, the cell of interest is determined as being in the cell state corresponding to the row "amount of paste is suitable," "amount of paste is small (1)," or "amount of paste is small (2)," and then, determined as containing no micro-defects, and further, the processing operation proceeds to the next step S23. In contrast, if the area "B" is not less than the threshold value, the cell of interest is determined as being in the cell state corresponding to the row "amount of paste is lacking" or "cell is empty" and the processing operation proceeds to step S22, and then, a flag indicative of inclusion of micro-defects is set in the cell, and further, the processing operation proceeds to step S23.

Additionally, when the cell of interest is in the cell state corresponding to the row "amount of paste is excessive," the area of the region 25 is measured and based on the measured result, the extent to which the excessively applied paste is being applied to associated portions of the cell is evaluated, and then, whether the cell includes micro-defects is determined. Furthermore, when the cell is in the cell state corresponding to the row "paste has flowed into cell," the width (the amount of displacement) and the area of a portion over which a paste has flowed are measured and whether the cell of interest includes micro-defects is determined. Still furthermore, when the cell is in the cell state corresponding to the drawing "abnormal substance," the area and the length of the abnormal substance are measured and whether the cell of interest includes micro-defects is determined.

In step S23, whether steps S21 and S22 have been performed on all cells to be inspected is determined and when the steps have not been performed on all cells, the processing operation returns to step S21, and when the steps have been performed on all cells, the processing operation proceeds to step S24.

Then, as shown in step S24, the number of flags indicating inclusion of micro-defects and set in step S22 is summed and counted. Thereafter, as shown in step S25, the counted number of flags indicative of inclusion of micro-defects is compared with a previously determined threshold value and when the number of flags indicative of inclusion of micro-defects is less than the threshold value, the substrate of interest is determined as being "in a favorable one of states indicative of inclusion/exclusion of micro-defects," and the processing operation proceeds to step S27. When the number of flags indicative of inclusion of micro-defects is not less than the threshold value, the substrate of interest is determined as being "in an unfavorable one of states indicative of inclusion/exclusion of micro-defects," and the processing operation proceeds to step S26, and then, a flag indicating the substrate is defective is set. Thereafter, the processing operation proceeds to step S27.

Subsequently, as shown in step S27, whether the processing operations shown in steps S19 to S26 have been performed on all types of defects is determined and when the processing operations have not yet been performed on all types of defects, the processing operation returns to step S19, and the processing operations shown in steps S19 to S26 are performed on the remaining types of defects. In addition, the processing operations shown in steps S19 to S26 have been performed on all types of defects, the processing operation proceeds to step S28.

Thereafter, as shown in step S28, final determination is performed based on results obtained by the aforementioned inspection operation. That is, whether flags indicating cells include macro-defects and set in step S18, and flags indicating cells include micro-defects and set in step S26 are present or not is determined, and when even only one flag is found to be present, an inspection result is determined to be "NG," and when no flag is founds an inspection result is determined to be "OK." Thus, the inspection operation shown in step S2 of FIG. 5 is terminated.

When the inspection result has been determined to be "NG," the substrate of interest is abandoned and is not subjected to subsequent steps any more. When the inspection result has been determined to be "OK," the substrate of interest is subjected to step S3 of FIG. 5. Furthermore, regardless of the inspection results, i.e., "OK" and "NG," when defects have been found in the substrate, the information indicative of the defects is fed back to the step, shown in step S1, of applying a phosphor paste of red material.

A detailed method for feeding back information indicative of defects to corresponding steps is performed as follows. For example, when the same type of defects have been consecutively found in the same portion (cell or area) of PDP in process steps for manufacture of PDP, an inspection apparatus (refer to FIG. 4) activates an alarm and outputs a command that stops a printing apparatus from performing a cyclic operation.

Figure 1:
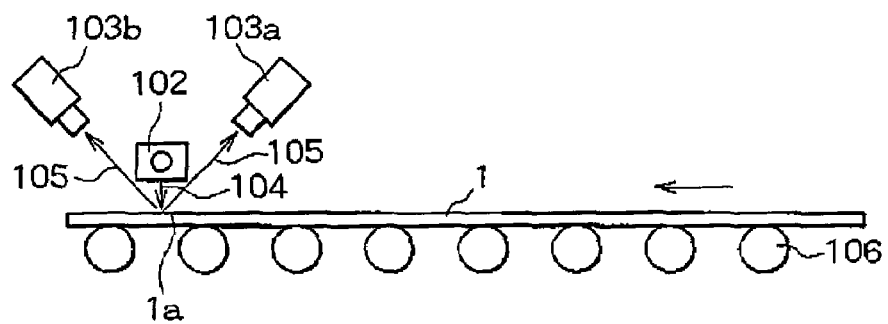
FIG. 1 is a side view of a conventional inspection apparatus for inspecting a phosphor layer.
Figure 2:
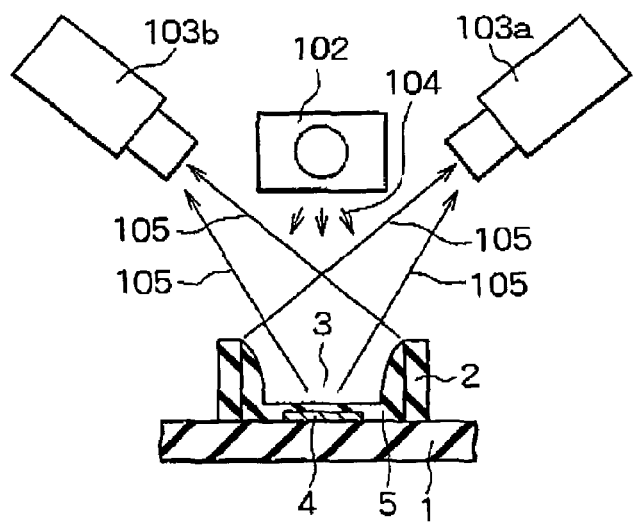
FIG. 2 is a partially enlarged cross sectional view of the conventional inspection apparatus for inspecting a phosphor layer.
Figure 3:
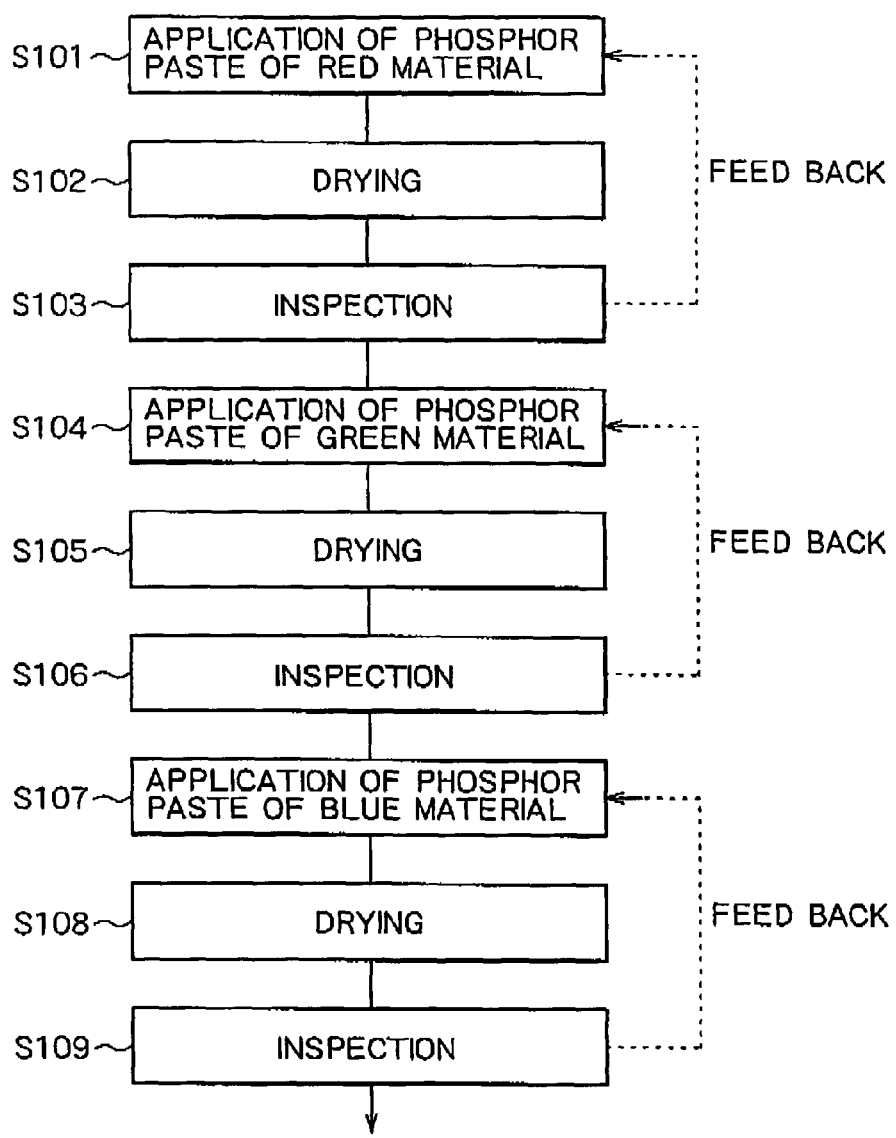
FIG. 3 is a flow chart diagram illustrating process steps of forming a phosphor layer, which process steps are included in conventional manufacturing steps for PDP.

Thereafter, as shown in step S3 of FIG. 5, the phosphor paste 5a (refer to FIG. 6) of red material is dried. The drying operation is, for example, carried out such that the substrate 1 is transferred to a dry oven and the substrate is gradually heated to a temperature of, for example, 130° C., and then, gradually cooled down to the room temperature. A necessary time interval over which heating starts and cooling terminates is set to, for example, be 30 minutes. This allows the phosphor paste 5a of red material to be dried and hardened, resulting in formation of the phosphor layer 5 (refer to FIG. 2).

Then, as shown in step S4, a phosphor paste of second color (e.g., green) material is applied to a cell column adjacent the cell column on which the red phosphor layer is formed. In this case, the phosphor paste of second color material is applied using the same method as that employed to apply the phosphor paste of red material and shown in step S1, for example, using printing techniques.

Thereafter, as shown in step S5, whether the phosphor paste is normally being applied to associated portions is inspected. The inspection operation is performed in the same way as that employed in an inspection method for inspecting a phosphor paste of red material, which inspection method is shown in step S2 and steps S11 to S28 (refer to FIGS. 7 and 8). Note that in the inspection operation, shown in step S5, for inspecting a phosphor paste of green material, the data indicative of results obtained in step S2 by inspecting the phosphor paste of red material is referred. Accordingly, for example, when the phosphor paste of red material has flowed into a cell to which a phosphor paste of green material will be applied in a subsequent step and the phosphor paste of green material is applied overlying the phosphor paste of red material in the cell, the cell of interest can be identified as being a nonnormal cell. Note that the cell of interest becomes a cell that causes color mixture.

When the inspection result obtained in step S5 has been determined to be "NG," the substrate of interest is abandoned and is not subjected to subsequent steps any more. When the inspection result has been determined to be "OK," the substrate is subjected to step S6. Furthermore, regardless of the inspection results, i.e., "OK" and "NG," when defects have been found in the substrate, the information indicative of the defects is fed back to the step, shown in step S4, of applying a phosphor paste of green material.

Thereafter, as shown in step S6, through use of a method similar to that shown in step S3, a phosphor paste of green material is dried to form a green phosphor layer.

Subsequently, as shown in step S7, a phosphor paste of third color (e.g., blue) material is applied to a cell column between the cell column on which the red phosphor layer is formed and the cell column on which the green phosphor layer is formed. In this case, the phosphor paste of third color material is applied using the same method as that employed to apply the phosphor paste of red material and shown in step S1, for example, using printing techniques.

Thereafter, as shown in step S8, whether the phosphor paste is normally being applied to associated portions is inspected. The inspection operation is performed in the same way as those employed in inspection methods each for inspecting a phosphor paste of red material and inspecting a phosphor paste of green material, which inspection methods are shown in steps S2, S5 and steps S11 to S28 (refer to FIGS. 7 and 8). Note that in the inspection operation, shown in step S8, for inspecting a phosphor paste of blue material, the data indicative of results obtained in step S2 by inspecting the phosphor paste of red material and the data indicative of results obtained in step S5 by inspecting the phosphor paste of green material are referred. When the inspection results obtained in steps S2, S5 have been determined to be "NG," the substrate of interest is abandoned and is not subjected to subsequent steps any more. When the inspection results have been determined to be "OK," the substrate is subjected to step S9. Furthermore, regardless of the inspection results, i.e., "OK" and "NG," when defects have been found in the substrate, the information indicative of the defects is fed back to the step, shown in step S7, of applying a phosphor paste of blue material.

Thereafter, as shown in step S9, through use of a method similar to that shown in step S3, the phosphor paste of blue material is dried to form a blue phosphor layer. Then, the phosphor layers emitting light of individual colors are fired. Thus, the phosphor layers emitting light of the primary colors, i.e., red, green and blue, can be formed.

Through the above-described steps, a front substrate of PDP is manufactured. Then, the front substrate and the rear substrate are aligned to overlap each other and attached together with an adhesive sealing material. Thereafter, gas contained in discharge spaces formed between the front substrate and the rear substrate is evacuated, and the discharge spaces are filled with discharge gas. Thus, a PDP can be manufactured.

The method according to the embodiment is performed such that in the step of manufacturing a rear substrate, a phosphor paste in the form of paste is applied to the surface of the substrate and the side surfaces of the barrier ribs, and prior to drying the phosphor paste, whether the phosphor material is normally being applied to associated portions is inspected. Then, based on the results obtained by the inspection operation, whether the phosphor layer 5 will normally be formed or not is determined prior to formation of phosphor layer. This allows the results obtained by determination of whether the phosphor layer 5 will normally be formed or not to quickly be fed back to the application step of applying a phosphor material.

Furthermore, according to the method employed in the embodiment, an LED is used as a light source and light from the LED is directed to and reflected by phosphor paste, and then, the phosphor material is inspected based on the reflection pattern of the reflected light. Accordingly, there is no need to use ultraviolet rays. This eliminates the need for an ultraviolet ray lamp conventionally required, an apparatus for preventing an operator from directly viewing ultraviolet rays and an equipment for preventing generation of ozone, thereby allowing the cost and the running cost of the associated apparatus to become lower in comparison with the case where the conventional method is employed to inspect a phosphor material. Furthermore, according to the method employed in the embodiment, the phosphor paste is observed through their liquid surface and therefore, can be viewed from a direction vertical to the surface of the substrate, which operation is different from that employed in the case where a phosphor layer is observed after drying of phosphor material. Accordingly, the inspection operation employed in the embodiment can be performed by just providing a CCD camera directly above a portion to be inspected on the substrate, reducing the number of CCD cameras to half the number of CCD cameras that are required in the conventional inspection method using ultraviolet rays. This allows investment cost to further be reduced.

Moreover, viewing the pattern of reflected light makes it possible to distinguish pinholes from abnormal substances or vice versa, which operation has been difficult to perform in the case where the conventional inspection method using ultraviolet rays is employed.

Still furthermore, according to the method employed in the embodiment, determination of whether a cell includes macro-defects is performed in steps S15 to S18 of FIG. 7 and determination of whether a cell includes micro-defects is performed in steps S19 to S28 of FIG. 8. This allows micro-defects as defects included in each of a plurality of cells to be detected and at the same time, permits macro-defects as defects included in each block consisting of a plurality of cells to be detected. As a result, uneven display or color distortion on a screen of PDP can be identified as a defect, allowing determination operation to be performed so as to produce results nearly equivalent to those obtained by visual determination.

Still furthermore, in the inspection step, shown as step S5 of FIG. 5, of inspecting a phosphor paste of second color (green) material, the inspection results obtained by inspecting a phosphor paste of first color (red) material and shown in step S2 are added to the inspection results obtained in step S5 and then whether the substrate of interest is normally being formed is totally determined. Moreover, in the inspection step, shown as step S8, of inspecting a phosphor paste of third color (blue) material, whether the substrate of interest is normally being formed is totally determined based on the inspection results obtained in steps S2, S5 and S8. Accordingly, a cell that cannot easily be identified as a non-normal cell through a single inspection step can be identified as a non-normal cell. In more detail, for example, a certain cell, which is characterized in that a phosphor paste of red material had flowed into the certain cell to which a phosphor paste of green material is to be applied in a subsequent step and the phosphor paste of green material has been applied on the top of the certain cell, can be identified as a non-normal cell.

Additionally, since visible light radiated by an LED is light configured to have a wavelength range so as to be able to prevent phosphors of phosphor paste from being excited and emitting light, the reflection pattern produced only by reflected light can accurately be captured without interference from the excited light.

It should be appreciated that although the method according to the embodiment has been explained as a method in which a phosphor paste is applied by printing techniques and a sequential operation (application→inspection→drying) is repeated for individual colors, the present invention is not limited to the aforementioned method, but may employ another method in which, for example, phosphor pastes corresponding individual colors are applied on a substrate color by color and after phosphor pastes of three primary color material are applied, an inspection operation is performed one time on the phosphor pastes and the phosphor pastes are dried. When employing the aforementioned method, an inspection and drying each may be performed one time, allowing a PDP to be manufactured with high efficiency.

Furthermore, although the method according to the embodiment has been explained as a method in which a first color is defined to be red (R), a second color is defined to be green (G), a third color is defined to be blue (B), and phosphor layers are formed in the order of red, green and blue, the present invention is not limited to the aforementioned method. The invention may employ another method in which, for example, phosphor layers are formed in the order of blue, red and green. Moreover, although the method according to the embodiment has been explained as a method in which a rib structure has a rectangular lattice-like layout, the present invention is not limited to the aforementioned method, but may employ another method in which, for example, a rib structure has a stripe-like or delta-like layout.

What is claimed is:

1. A method for manufacturing a plasma display panel, comprising:
    a step for forming barrier ribs on a surface of an insulating substrate in order to separate a plurality of cells from one another;
    an applying step for applying a phosphor material in the form of paste to each of said cells by covering said surface of said insulating substrate and side surfaces of said ribs with said phosphor material;
    an inspecting step; and
    a drying step for drying the phosphor material paste,
    wherein said inspecting step determines whether an amount of said phosphor material in each of said cells is equal to or less than a predetermined amount based on a size of an area of a surface of said phosphor material that produces a maximum intensity of a reflected light when visible light is radiated onto a whole surface of said phosphor material before said drying step.

2. The method for manufacturing a plasma display panel according to claim 1, wherein said inspecting step further determines whether or not any one of said plurality of cells includes a pinhole or an abnormal substance, and whether or not said phosphor material flows into a cell to which said phosphor material is not yet applied so far.

3. The method for manufacturing a plasma display panel according to claim 1, wherein said inspecting step comprises the steps of:
    detecting a micro-defect defined as a defect included in any one of said plurality of cells; and
    detecting a macro-defect defined as a defect included in any one of blocks each comprising a plurality of cells.

4. The method for manufacturing a plasma display panel according to claim 1, wherein said applying step is performed based on a result obtained by said inspecting step performed for another plasma display panel manufactured before.

5. The method for manufacturing a plasma display panel according to claim 1, wherein said phosphor material includes three kinds of materials emitting different colors, and said three kinds of materials are applied to different cells in first, second and third application steps, respectively, and said inspecting step is performed in such a manner that after the first application step and before the second application step, one of said three kinds of materials applied in the first application step is inspected, and after the second application step and before the third application step, another one of said three kinds of materials applied in the second application step is inspected with an inspection result of said material applied in the first application step being taken into account, and after the third application step, a last one of said three kinds of materials applied in the third application step is inspected with inspection results of said materials applied in the first and second application steps being taken into account.

6. The method for manufacturing a plasma display panel according to claim 1, wherein said applying step is performed by printing techniques.

* * * * *